(12) United States Patent
Delansorne et al.

(10) Patent No.: US 8,481,514 B2
(45) Date of Patent: Jul. 9, 2013

(54) THERAPEUTICAL USES OF INECALCITOL

(75) Inventors: Rémi Delansorne, Paris (FR); Jean-François Dufour-Lamartinie, Paris (FR)

(73) Assignee: Hybrigenics SA, Paris (FR)

( * ) Notice: Subject to any disclaimer, the term of this patent is extended or adjusted under 35 U.S.C. 154(b) by 308 days.

(21) Appl. No.: 12/782,301

(22) Filed: May 18, 2010

(65) Prior Publication Data

US 2011/0015276 A1 Jan. 20, 2011

Related U.S. Application Data

(60) Provisional application No. 61/179,906, filed on May 20, 2009.

(51) Int. Cl.
*A61K 31/59* (2006.01)

(52) U.S. Cl.
USPC .......................................... 514/167; 514/168

(58) Field of Classification Search
USPC .......................................... 514/729, 167, 168
See application file for complete search history.

(56) References Cited

FOREIGN PATENT DOCUMENTS

EP 0972762 1/2000

OTHER PUBLICATIONS

Hybrigenics: "Promising interim results from Hybrigenics' Inecalcitol Phase II in combination with Taxotere (R) for hormone refractory prostate cancer" [Online] Apr. 19, 2009, XP002592440, Medical News Today, Retrieved from the Internet URL: http://www.medicalnewstoday.com/articles/146552.php> [retrieved on Jul. 8, 2010].
Eelen et al, "Superagonistic action of 14-epi-analogs of 1, 25-dihydroxyvitamin D explained by vitamin D receptor-coactivator interaction", May 2005, pp. 1566-1573, vol. 67, No. 5, Molecular Pharmacology.
Verlinden et al, "Two novel 14-epi-analogues of 1, 25-dihydroxyvitamin D3 inhibit the growth of human breast cancer cells in vitro and in vivo" May 15, 2000, pp. 2673-2679, vol. 60, No. 10, Cancer Research.
Eelen et al, "Vitamin D analogs and coactivators" Jul. 1, 2006, pp. 2717-2721, vol. 26, No. 4A, Anticancer Research International Institute of Anticancer Research, Inc., GR.
Anonymous: "Hybrigenics in-licences Merk KGaA's inecalcitol" [Online], Feb. 8, 2006, XP002592443 Biocentury Retrieved from the Internet URL: http://www.biocentury.com/dailynews/company/2006/02-08/hybrigenics-in-licenses-merck-kgaas-inecalcitol> [retrieved on Jul. 9, 2010].
Holick, Michael F., "Resurrection of vitamin D deficiency and rickets", Aug. 2006, pp. 2062-2072, vol. 116, No. 8, The Journal of Clinical Investigation.
Holick, Michael F., "Vitamin D: Important for Prevention of Osteoporosis, Cardiovascular Heart Disease, Type 1 Diabetes, Autoimmune Diseases, and Some Cancers", Oct. 2005, pp. 1024-1027, vol. 98, No. 10, Southern Medical Journal.
Verlinden et al, "Interaction of Two Novel 14-Epivitamin $D_3$ Analogs with Vitamin $D_3$ Receptor-Retinoid X Receptor Heterodimers on Vitamin $D_3$ Responsive Elements", 2001, pp. 625-638, vol. 16, No. 4, Journal of Bone and Mineral Research.

*Primary Examiner* — Raymond Henley, III

(74) *Attorney, Agent, or Firm* — B. Aaron Schulman, Esq.; Terry L. Wright, Esq.; Stites & Harbison, PLLC

(57) ABSTRACT

The present invention thus concerns a method for treating and/or preventing rickets, osteoporosis, osteomalacia, psoriasis, autoimmune diseases such as multiple sclerosis or type I diabetes, hyperparathyroidism, benign prostate hyperplasia, any type of cancer or any vitamin D relevant disease comprising administering inecalcitol at doses comprised between 1 mg/day and 100 mg/day to a human patient in need thereof.

24 Claims, 4 Drawing Sheets

THERAPEUTICAL USES OF INECALCITOL

CROSS REFERENCE TO RELATED APPLICATIONS

This application claims benefit of U.S. Provisional Application No. 61/79,906 filed May 20, 2009 (which is hereby incorporated by reference).

Vitamin D is a group of prohormones, the two major forms of which are vitamin $D_2$ (or ergocalciferol) and vitamin $D_3$ (or cholecalciferol). Vitamin D, its metabolites and analogues have potent effects on calcium and phosphate metabolism and can therefore be used for prevention and therapy of vitamin D deficiency, such as rickets, and other disorders of plasma and bone mineral homeostasis such as osteoporosis and osteomalacia. Moreover, vitamin D receptors and vitamin D activity have also been documented in numerous other tissues and cells, where they are also known to be involved in cell proliferation and differentiation. Vitamin D also affects the immune system as vitamin D receptors are expressed in several white blood cells including monocytes, macrophages and T and B lymphocytes.

These so-called non-calcemic effects of vitamin D lead to consider the possible use of vitamin D derivatives for various therapeutic applications such as disorders of the immune system, hormone secretion, cell differentiation or cell proliferation. In particular, such compounds may be useful in the therapy of disorders characterized by increased cell proliferation, such as psoriasis and/or cancer. In particular, 1,25 $(OH)_2$-vitamin $D_3$, the active metabolite of vitamin $D_3$ named calcitriol, is known to inhibit the proliferation of many cancer cells lines of various origins in vitro and to slow the progression of various tumor xenografts in vivo. The major drawback related to the use of this compound is its hypercalcemic effect, which prevents the application of pharmacologically active doses. The toxic effects of calcitriol and all vitamin D analogues are the consequences of hypercalcemia leading to micro-crystallization of calcium in various tissues, or inducing disorders of muscle contractility. Hypercalcemia may thus cause death by impairing contraction of the heart (cardiac arrest) or by accumulation of calcium micro-crystals in renal tubules (kidney failure). Hypercalcemia may also cause arthritis or cataract (deposits of micro-crystals in the joints or in the eye lens, respectively) or muscle weakness (impaired contractions). It is therefore of utmost importance for a vitamin D analogue to be used in therapeutics without the risk of inducing hypercalcemia.

A large number of analogues of calcitriol displaying a clear dissociation between anti-proliferative and calcemic effects have been reported. In particular, EP 0 707 566 B1 discloses a number of calcitriol analogues such as 14-epianalogues. Among these 14-epianalogues of calcitriol is inecalcitol of formula:

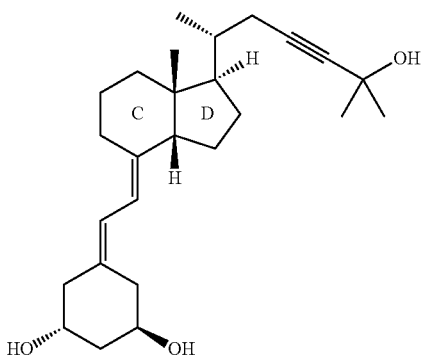

Inecalcitol is the international non-proprietary name for 19-nor-9,10-seco-14βH-cholesta-5(Z),7(E)-dien-23-ino-1α, 3β,25-triol-23-yne ($C_{26}H_{40}O_3$).

Inecalcitol is a synthetic derivative of calcitriol, the natural active metabolite of vitamin $D_3$. Eelen et al. (Molecular Pharmacology 67, 1566-1573, 2005) and Verlinden et al (Journal of Bone and Mineral Research, volume 16(4), 625-638, 2001) showed the enhanced antiproliferative and markedly lower calcemic effects of inecalcitol compared with calcitriol. Verlinden et al. (Cancer Research 60(10), 2673-2679, 2000) also reported the in vitro and in vivo activity of inecalcitol in inhibiting the growth of human breast cancer cells. This profile has positioned inecalcitol as an effective drug candidate, initially for the treatment cancer.

Considering the hypercalcemic effect of vitamin D and its analogues, it has been common practice to administer low doses of these compounds, or frequency of administration lower than once a day. As a result, vitamin D or its analogues are administered at doses generally much lower than 200 μg/day, and often every other day or once a week. In particular, the approved dose of calcitriol for vitamin D deficiency is 0.25 or 0.5 μg/day and the tested dose for calcitriol in cancer clinical trial was 45 μg/patient once a week; in the case of seocalcitol, the tested dose in cancer clinical trials was 10 μg/day/patient; for seocalcitol in clinical trials for benign prostate hyperplasia, the tested dose was 150 μg/day/patient; for the treatment of hypersecretion of parathormone (hyperparathyroidism), paricalcitol is approved at the maximum dosage of 2 μg/day or 4 μg every other day, and doxercalciferol at the maximum dosage of 3.5 μg/day or 20 μg every other day.

It is thus desirable to provide derivatives of vitamin D which are less toxic and can thus be administered at high pharmacologically active doses.

EP 0 707 566 B1 merely mentions a vitamin D analogue dose of 0.1 to 500 μg/g relative to the weight of the topical formulation to be applied on the skin to treat psoriasis. Verlinden et al (Cancer Research, supra) merely mentioned an inecalcitol dose of 80 μg/kg/every other day for administration in mice and are silent in respect of administration in human patients.

Further, in order to achieve the highest possible therapeutic effect from the active ingredient, it is desirable to increase the administered doses, without inducing side effects, such as hypercalcemia with all its deleterious consequences described above.

It has now been surprisingly discovered that inecalcitol was devoid of hypercalcemic effect at doses generally considered to be too toxic for all other known vitamin D analogues.

The present invention thus concerns a method for treating and/or preventing rickets, osteoporosis, osteomalacia, psoriasis, autoimmune diseases such as multiple sclerosis or type I diabetes, hyperparathyroidism, benign prostate hyperplasia, any type of cancer or any vitamin D associated disease, in particular cancer, comprising administering inecalcitol at doses comprised between 1 mg and 100 mg to a human or animal patient in need thereof.

The present invention also concerns inecalcitol for use for treating and/or preventing rickets, osteoporosis, osteomalacia, psoriasis, autoimmune diseases such as multiple sclerosis or type I diabetes, hyperparathyroidism, benign prostate hyperplasia, any type of cancer or any vitamin D associated disease, in particular cancer, for administration at doses comprised between 1 mg and 100 mg to a human or animal patient in need thereof.

Said administration dose is preferably comprised between 1.5 mg and 20 mg.

According to a preferred embodiment, the method of the invention comprises administering inecalcitol at doses comprised between 1.5 mg and 20 mg for the treatment and/or prevention of the above disorders, particularly any type of cancer, without inducing increased calcemia in the treated patient.

According to another embodiment, the method of the invention may comprise the administration of said doses of inecalcitol, at a frequency comprised between every three days up to three times a day, such as every three days, every other day (qod), once-a-day (qd), twice-a-day (bid) or three times a day (tid). Preferably, the administration may take place every other day, once a day or twice-a-day.

According to a further embodiment, the method of the invention also comprises the administration of one or more further active ingredient, selected from anti-osteoporotic agents, immunomodulatory agents, anti-inflammatory agents, anti-psoriatic agents, anti-hormonal agents, antiproliferative agents or anti-cancer agents.

Preferably, said anti-cancer agent is chosen from taxoid derivatives, in particular paclitaxel or docetaxel, or a platinum derivative in particular carboplatin, oxaliplatin or satraplatin. Said administration may be simultaneous, separate or sequential with that of inecalcitol.

According to another embodiment, the method of the invention is to treat various forms of cancers, including tumors or leukemia. Cancers of breast, prostate, lung, colon, bladder, brain, stomach, kidney, liver, ovary, mouth, skin, intestine, uterine, head and neck, throat and blood cancers are encompassed herein, particularly prostate cancer.

According to another embodiment, the method of the invention is to treat non-cancerous hyperproliferative disorders of the skin, particularly psoriasis, by administration of inecalcitol at high dose, alone or in combination with systemic oral or parenteral treatments of psoriasis on the market or in development such as acitretine and retinoids in general, cyclosporine, voclosporine, sirolimus, tacrolimus, methotrexate and immunosuppressants or immunomodulators in general, alefacept, etanercept, infliximab adalimumab, certolizumab, golimumab and anti-Tumor Necrosis Factor-alpha therapeutics in general, ustekinumab, briakinumab and anti-interleukines therapeutics in general, apremilast, MAP Kinase inhibitors, A3 adenosine agonists, and the like (Melnikova, Nature reviews drug discovery 2009, 8, 767-768).

According to another embodiment, the method of the invention is to treat the symptoms, prevent relapses or prolong remissions of multiple sclerosis, by administration of inecalcitol at high dose, alone or in combination with systemic oral or parenteral treatments of multiple sclerosis on the market or in development such as interferons alpha and beta and their various isoforms, mitoxantrone, laquinimod, fingolimod and immunosuppressants or immunomodulators in general, natalizumab, daclizumab, copaxone, cladribine, teriflunomide, and the like.

Inecalcitol may be preferably administered by oral route.

According to another object, the present invention also relates to the above-mentioned therapeutic treatment methods comprising the administration of inecalcitol with a pharmaceutically acceptable carrier or excipient to a patient in the need thereof.

When used herein, inecalcitol refers to inecalcitol or its pharmaceutically acceptable salts thereof.

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of inecalcitol, which is required to achieve the desired biological effect, will vary depending upon a number of factors, including the dosage of the drug to be administered, the type of disease, the disease state of the patient and the route of administration.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles. The use of such carriers for pharmaceutical active substances is well known in the art.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with rickets, osteoporosis, osteomalacia, psoriasis, autoimmune diseases such as multiple sclerosis or type I diabetes, hyperparathyroidism, benign prostate hyperplasia, any type of cancer or any vitamin D associated disease. Preferably, the patient is a human.

In general terms, the preferred dosage of drug to be administered is likely to depend on such variables as the type and extent of progression of the disease or disorder, the overall health status of the particular patient, the relative biological efficacy of the compound selected, and formulation of the compound excipient, and its route of administration and will generally exceed 1 mg/day per patient.

Inecalcitol is capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition.

Inecalcitol can be formulated into pharmaceutical compositions by admixture with one or more pharmaceutically acceptable excipients.

The compositions may conveniently be administered in unit dosage form and may be prepared by any of the methods well known in the pharmaceutical art, for example, as described in *Remington: The Science and Practice of Phar-* macy, 20th ed.; Gennaro, A. R., Ed.; Lippincott Williams & Wilkins: Philadelphia, Pa., 2000. The usual unit doses for oral administration of vitamin D analogues are soft gelatine capsules containing medium chain triglycerides from fractionated coconut oil in which the compound is dissolved like for calcitriol, doxercalciferol or paricalcitol.

EXAMPLE 1

Figure 1:
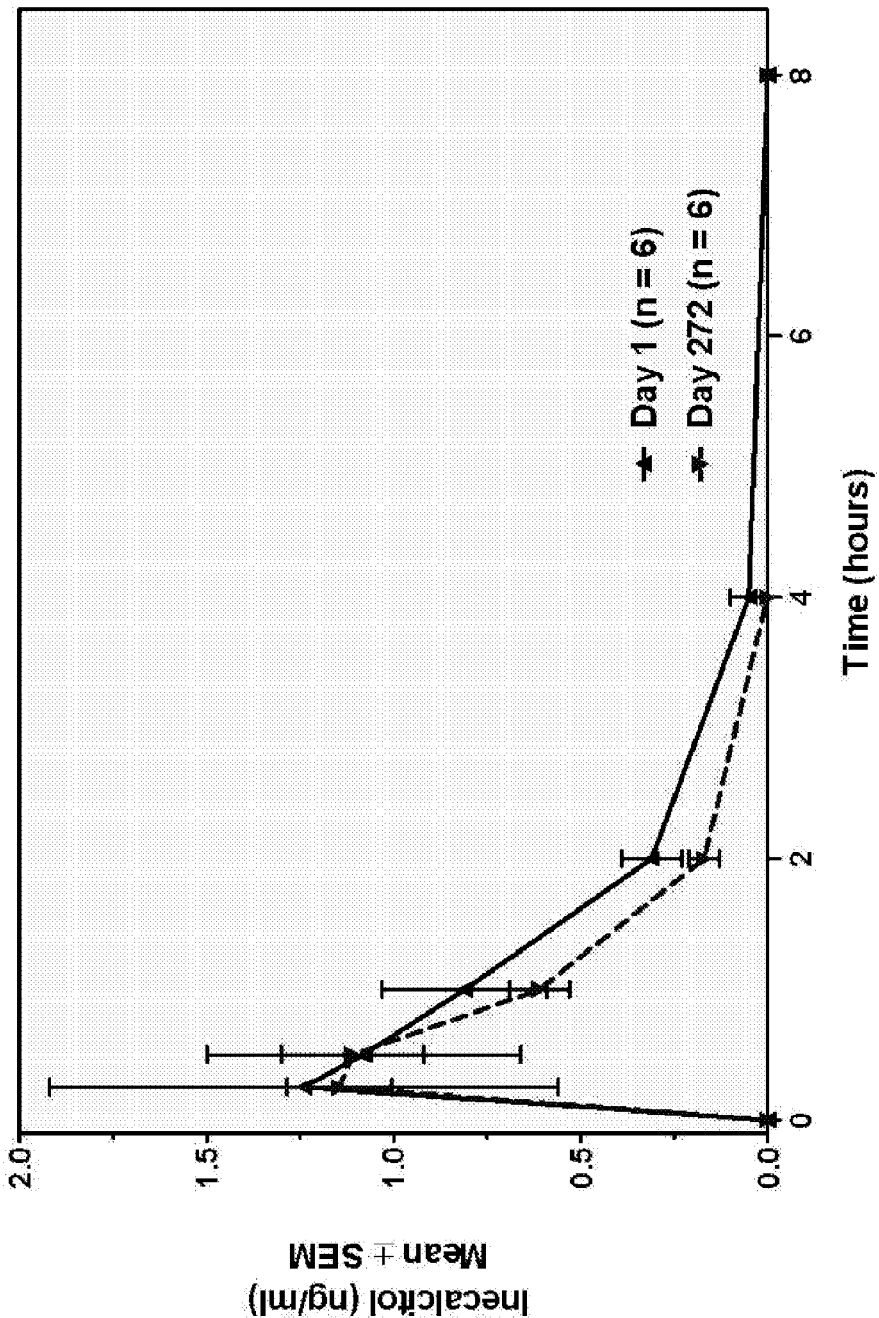
FIG. 1 illustrates the mean plasma concentrations vs time obtained during a 9-month toxicology study on once-a-day oral inecalcitol performed in male mature monkeys.

9-Month Toxicology and Toxicokinetic Study of Once-a-Day Oral Inecalcitol in Monkeys During a 9-month toxicology study in male mature cynomolgus monkeys by daily oral administration of inecalcitol, no hypercalcemia and no toxic effects were observed, even at the highest tested dose of 1.8 milligram (mg) per day per monkey, despite a consistently high peak exposure to inecalcitol in blood. On FIG. 1, mean plasma concentrations of inecalcitol are plotted vs. time on the first day of the study and close to its end, at day 272. The mean toxicokinetic profiles are almost superimposable, with a mean peak of about 1.2 ng/ml achieved as soon as 15 minutes after oral intake, and a steady disappearance from circulation within 4 hours. Higher doses, not tested in the study, may also be devoid of hypercalcemia and of toxic effects since the maximal tolerated dose has not been reached. In the table below, plasma calcium levels (in mmoles/L, mean±s.e.m.) at different time points during the study did not show any difference between control and treated monkeys.

|  | Study Day | | | |
| --- | --- | --- | --- | --- |
|  | Day −12 | Day 85 | Day 175 | Day 268 |
| Controls (n = 6) | 2.48 ± 0.02 | 2.59 ± 0.06 | 2.46 ± 0.05 | 2.53 ± 0.03 |
| Treated (n = 6) | 2.54 ± 0.11 | 2.53 ± 0.03 | 2.49 ± 0.05 | 2.51 ± 0.05 |

EXAMPLE 2

Figure 2:
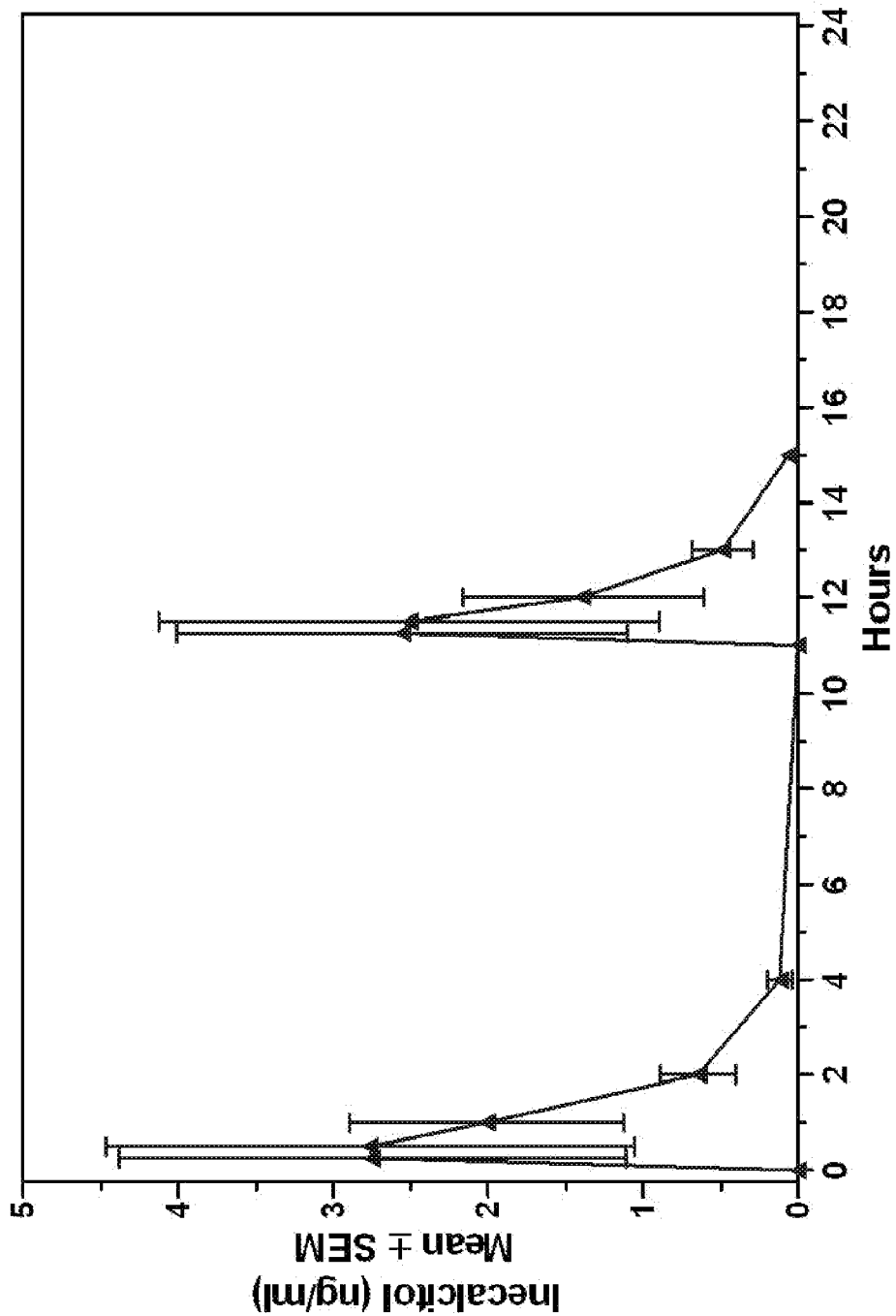
FIG. 2 illustrates the mean plasma concentrations vs time obtained during a 2-week toxicology study on twice-a-day oral inecalcitol performed in male juvenile monkeys.

2-Week Toxicology and Toxicokinetic Study of Twice-a-Day Oral Inecalcitol in Monkeys During a 2-week toxicology study in male juvenile cynomolgus monkeys by twice daily oral administrations of inecalcitol, no hypercalcemia and no toxic effects were observed at the dosage of 2×1.6 milligram (mg) each day, despite a frequent exposure to very high plasma levels of inecalcitol. On FIG. 2, mean plasma concentrations of inecalcitol are plotted vs. time on the first day of treatment with two successive administrations of inecalcitol around 8 AM and 7 PM, i.e. about 11 hours apart. Two almost identical peaks were observed reaching 2.75 ng/ml and 2.50 ng/ml respectively. In both instances, inecalcitol levels returned to basal levels within 4 hours. In the table below, plasma calcium levels (in mmoles/L, mean±s.e.m.) were monitored in the same 4 animals for two weeks before and for two weeks during the treatment period. No significant changes in plasma calcium were observed.

|  | Study Day | | | |
| --- | --- | --- | --- | --- |
|  | Day −13 | Day −6 | Day 7 | Day 13 |
| Plasma Ca | 2.66 ± 0.088 | 2.61 ± 0.06 | 2.68 ± 0.15 | 2.76 ± 0.12 |

EXAMPLE 3

Dose Finding and Clinical Tolerance Study of Inecalcitol in Combination with Docetaxel-Prednisone Regimen in Hormone-Refractory Prostate Cancer (HRPC) Patients 3.1 Methods Escalating oral dosages of inecalcitol were combined to chemotherapy in naive HRPC patients. Safety was evaluated in groups of 3-6 patients receiving inecalcitol every other day (qod) or daily (qd) on a 21-day cycle in combination with intravenous docetaxel (75 mg/m2 q3w) and oral prednisone (5 mg bid). Patients (pts) received up to six cycles unless unacceptable toxicity or disease progression. Primary endpoint was dose limiting toxicity (DLT) defined as grade 3 hypercalcemia within the first cycle. Calcemia, creatininemia and complete blood counts were assessed weekly; biochemistry, electrocardiogram and prostate specific antigen (PSA) every 3 weeks. Efficacy endpoint was PSA response defined as ≧30% decline within 3 months.

Inecalcitol was given to patients in soft gelatine capsules of different sizes, shapes and strengths depending on the dose level studied: one, two or four 40 µg capsules (size 11, oblong shape) for administration of 40, 80 or 160 µg/day, respectively; three or six 100 µg capsules (size 4, round shape) for administration of 300 or 600 µg/day, respectively; five 200 µg capsules (size 7.5, oval shape) for administration of 1,000 µg/day; five 400 µg capsules (size 14, oblong shape) for administration of 2 mg/day, and four 1 mg capsules (size 14, oblong shape) for administration of 4 mg/day. In all the capsules, inecalcitol was present in the fill content as a solution in medium chain triglycerides from fractionated coconut oil at different concentrations depending on the capsule strengths.

3.2 Clinical Results

Eight dose levels: 40 µg (qd), 80 µg (qod,qd), 160 µg (qod,qd), 300 µg (qod,qd), 600 µg (qod,qd), 1,000 µg (qod,qd), 2 mg (qd) and 4 mg (qd) have been evaluated; 50 pts have been treated; 47 pts have completed 6 cycles. Median age was 71 years [range, 49-87], median Gleason score (Gs) 7 and median PSA 35.7 ng/mL [range, 0.9-962.4]. No increased calcemia was reported. Most adverse events (AE) were G1-2, asthenia (22 pts), constipation (15 pts), diarrhea (13 pts). G3-4 AEs were neutropenia (36 pts) lymphopenia (12 pts), asthenia (3 pts), arrhythmia (2 pts), general health deterioration (3 pts) and diarrhea (1 pt). All these AEs were related to docetaxel and none to inecalcitol. Of the 42 evaluable pts for PSA response within three months of treatment, 35 (83%) showed a PSA decline of more than 30%.

3.3. Pharmacokinetics of Inecalcitol in HRPC Patients

Figure 3:
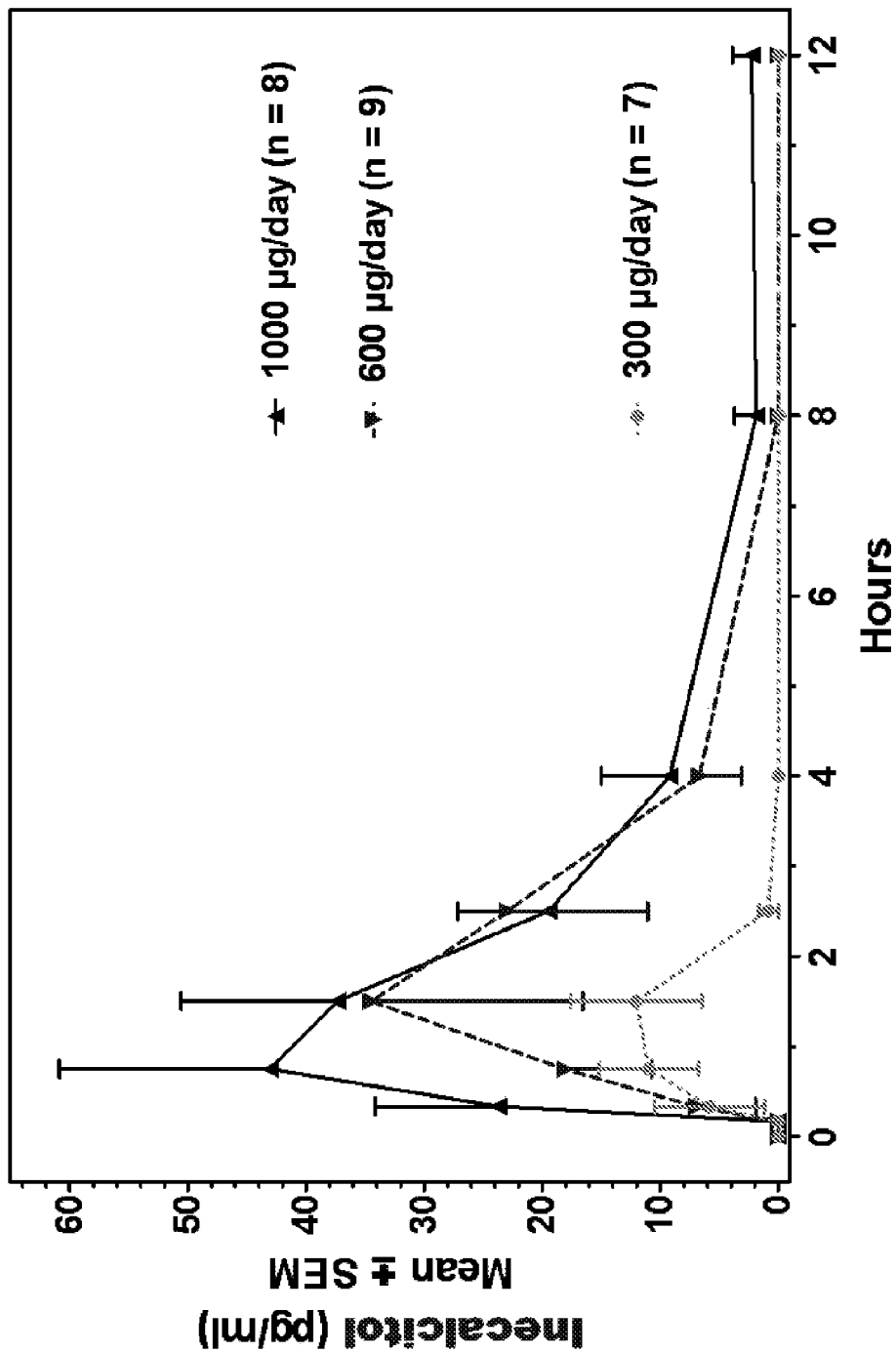
FIG. 3 illustrates the mean pharmacokinetic profiles obtained with 300, 600 and 1000 µg of oral inecalcitol administered to human patients.
Figure 4:
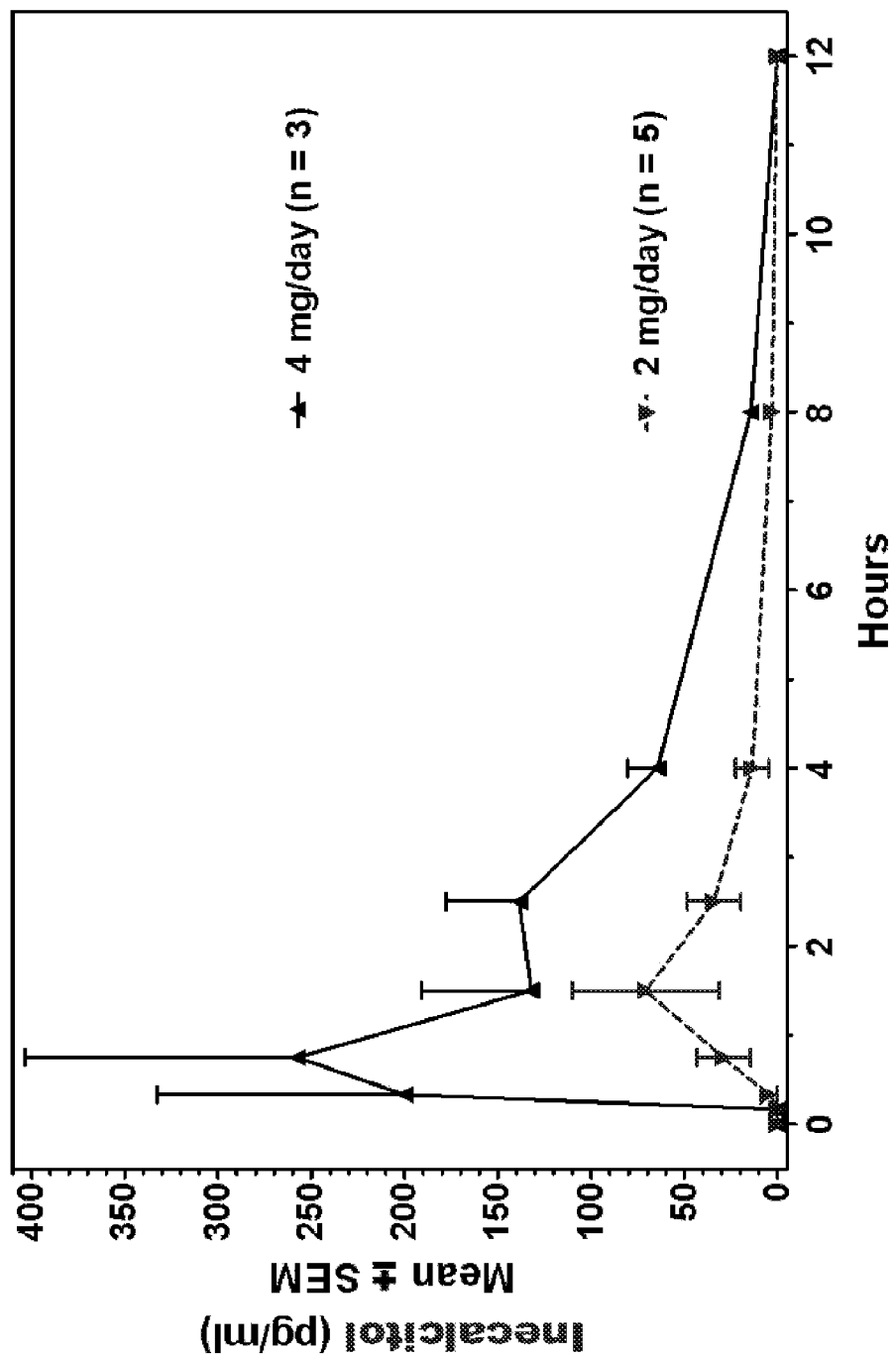
FIG. 4 illustrates the mean pharmacokinetic profiles obtained with 2 and 4 mg of oral inecalcitol administered to human patients The following examples are given as representative non-limiting illustrations of the invention.

Oral administration of inecalcitol at doses of 300 µg (qod, qd), 600 µg (qod,qd), 1000 µg (qod,qd), 2 mg (qd) or 4 mg (qd) to human hormone-refractory prostate cancer patients did not induce any hypercalcemia or any toxic effect. FIG. 3 shows the mean pharmacokinetic profiles obtained at the first three dose levels of 300, 600 and 1000 µg. Inecalcitol was assayed as unchanged circulating compound in the plasma by liquid chromatography followed by tandem mass spectrometry (LC/MS/MS). At 300 µg, peak values are barely detectable above the lower limit of quantitation achieved by the LC/MS/MS method, i.e. 10 pg/ml (0.01 ng/ml). At 600 µg and 1000 µg, mean peak values reached around 35 and 45 pg/ml (0.035 and 0.045 ng/ml) at 90 and 45 minutes, respectively. FIG. 4 shows the mean pharmacokinetic profiles with 2 mg and 4 mg of inecalcitol: mean peak values reached around 70 and 260 pg/ml (0.07 and 0.26 ng/ml) at 90 and 45 minutes respectively. In the four mean pharmacokinetic profiles obtained between 600 µg and 4 mg, the disappearance of inecalcitol was regular with an approximate half-life comprised between 1 and 1.5 hour.

The invention claimed is:

1. A method for treating rickets, osteoporosis, osteomalacia, psoriasis, autoimmune diseases, hyperparathyroidism, benign prostate hyperplasia, a cancer selected from the group consisting of breast cancer, prostate cancer, lung cancer, colorectal cancer, bladder cancer, brain cancer, stomach cancer, kidney cancer, liver cancer, ovary cancer, mouth cancer, skin cancer, intestinal cancer, uterine cancer, head and neck cancer throat cancer, blood cancer, thyroid cancer and pancreatic cancer or any vitamin D associated disease comprising administering inecalcitol at doses comprised between 1 mg and 100 mg to a patient in need thereof.

2. The method according to claim wherein said administration dose is comprised between 1.5 mg and 20 mg.

3. The method according to claim 1 which does not simultaneously induce increased calcemia in the treated patient.

4. The method according to claim 1 which comprises the administration of said doses of inecalcitol, at a frequency chosen from every three days, every other day (qod), once-a-day (qd), twice-a-day (bid) and three times a day (tid).

5. The method according to claim 4, wherein the administration is at a frequency chosen from every other day, once a day and twice a day.

6. The method according to claim 1 which also comprises the administration of one or more further active ingredient selected from anti-osteoporotic agents, immunomodulatory agents, anti-inflammatory agents, anti-psoriatic agents, anti-hormonal agents, antiproliferative agents and anti-cancer agents.

7. The method according to claim 6 wherein said further administration(s) is (are) simultaneous, separate or sequential with that of inecalcitol.

8. The method according to claim 1 which is for treating cancers, tumors or leukemia.

9. The method according to claim 1 wherein inecalcitol is administered by oral route.

10. The method according to claim 1 which is for treating psoriasis.

11. The method according to claim 1 wherein the autoimmune disease is multiple sclerosis.

12. The method according to claim 1 which is for treating hyperparathyroidism.

13. The method according to claim 1 which is for treating benign prostate hyperplasia.

14. The method according to claim 1 wherein the autoimmune disease is type I diabetes.

15. A method for treating rickets, osteoporosis, osteomalacia, psoriasis, autoimmune diseases, hyperparathyroidism, benign prostate hyperplasia, a cancer selected from the group consisting of tumors and leukemia or any vitamin D associated disease comprising administering inecalcitol at doses comprised between 1 mg and 100 mg to a patient in need thereof.

16. The method according to claim 15 wherein said administration dose is comprised between 1.5 mg and 20 mg.

17. The method according to claim 15 which does not simultaneously induce increased calcemia in the treated patient.

18. The method according to claim 15 which comprises the administration of said doses of inecalcitol, at a frequency chosen from every three days, every other day (qod), once-a-day (qd), twice-a-day (bid) and three times a day (tid).

19. The method according to claim 15 wherein the administration is at a frequency chosen from every other day, once a day and twice a day.

20. A method for treating rickets, osteoporosis, osteomalacia, psoriasis, autoimmune diseases, hyperparathyroidism, benign prostate hyperplasia, a cancer selected from the group consisting of breast cancers, prostate cancers, lung cancers, colon cancers, bladder cancers, brain cancers, stomach cancers, kidney cancers, liver cancers, ovary cancers, mouth cancers, skin cancers, intestine cancers, uterine cancers and throat cancers or any vitamin D associated disease comprising administering inecalcitol at doses comprised between 1 mg and 100 mg to a patient in need thereof.

21. The method according to claim 20 wherein said administration dose is comprised between 1.5 mg and 20 mg.

22. The method according to claim 20 which does not simultaneously induce increased calcemia in the treated patient.

23. The method according to claim 20 which comprises the administration of said doses of inecalcitol, at a frequency chosen from every three days, every other day (qod), once-a-day (qd), twice-a-day (bid) and three times a day (tid).

24. The method according to claim 20 wherein the administration is at a frequency chosen from every other day, once a day and twice a day.

* * * * *